United States Patent
Drake et al.

(10) Patent No.: US 11,826,074 B2
(45) Date of Patent: Nov. 28, 2023

(54) MEDICAL DEVICE DELIVERY SYSTEM WITH INTERNAL RIBS AND VENTS

(71) Applicant: Medtronic, Inc., Minneapolis, MN (US)

(72) Inventors: Ronald A Drake, St. Louis Park, MN (US); Lester O. Stener, Hudson, WI (US); Vladimir Grubac, Brooklyn Park, MN (US); Martin G. Hieb, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 518 days.

(21) Appl. No.: 16/921,512

(22) Filed: Jul. 6, 2020

(65) Prior Publication Data

US 2021/0030439 A1 Feb. 4, 2021

Related U.S. Application Data

(60) Provisional application No. 62/879,715, filed on Jul. 29, 2019.

(51) Int. Cl.
*A61B 17/34* (2006.01)
*A61M 25/00* (2006.01)
*A61N 1/372* (2006.01)
*A61N 1/05* (2006.01)

(52) U.S. Cl.
CPC ...... *A61B 17/3468* (2013.01); *A61N 1/37205* (2013.01); *A61B 2017/3454* (2013.01); *A61M 25/007* (2013.01); *A61N 1/0573* (2013.01)

(58) Field of Classification Search
CPC ............ A61M 25/0015; A61M 25/007; A61M 2025/0073; A61B 17/3468; A61B 2017/3454
See application file for complete search history.

(56) References Cited

U.S. PATENT DOCUMENTS

| | | | |
|---|---|---|---|
| 5,772,671 A * | 6/1998 | Harmon ............ | A61M 37/0069 604/60 |
| 7,223,263 B1 * | 5/2007 | Seno ................... | A61M 25/007 604/537 |
| 9,072,867 B2 * | 7/2015 | Malhi .................. | A61M 1/3653 |
| 9,526,522 B2 | 12/2016 | Wood et al. | |
| 10,112,045 B2 | 10/2018 | Anderson et al. | |
| 2012/0172690 A1 | 7/2012 | Anderson et al. | |
| 2015/0051615 A1 | 2/2015 | Schmidt et al. | |
| 2016/0263372 A1 * | 9/2016 | Wood ................... | A61N 1/3756 |
| 2017/0136231 A1 * | 5/2017 | Kelly ................... | A61N 1/0573 |
| 2020/0101279 A1 | 4/2020 | Drake et al. | |

FOREIGN PATENT DOCUMENTS

WO 2020069293 A1 4/2020

OTHER PUBLICATIONS

International Search Report and Written Opinion of International Application No. PCT/US2020/042876, dated Jul. 21, 2020, 9 pp.

* cited by examiner

*Primary Examiner* — Majid Jamialahmadi
(74) *Attorney, Agent, or Firm* — Shumaker & Sieffert, P.A.

(57) ABSTRACT

In some examples, a medical device delivery system includes a device cup configured to retain the medical device at the distal end of a catheter, the cup having a cylindrical body defining at least one vent hole extending from an exterior surface of the body to an interior surface of the body, and at least one internal rib extending inwardly from the interior surface, the rib configured to contact the medical device.

25 Claims, 15 Drawing Sheets

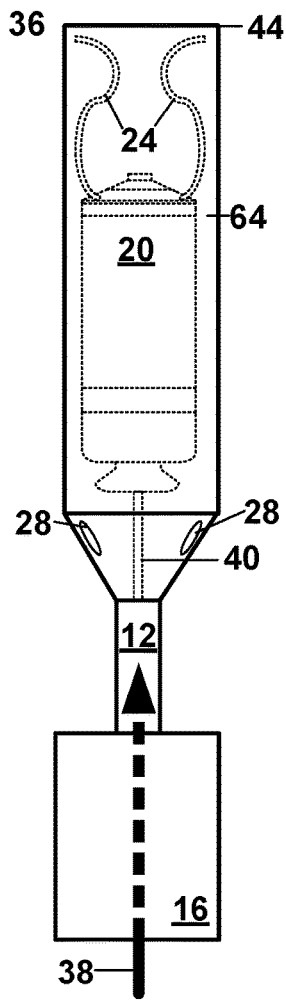
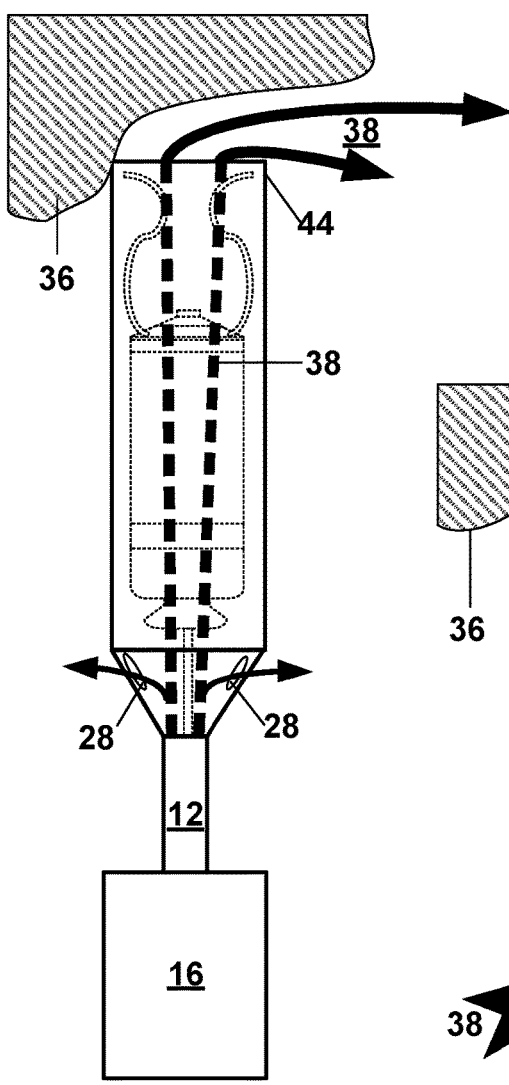
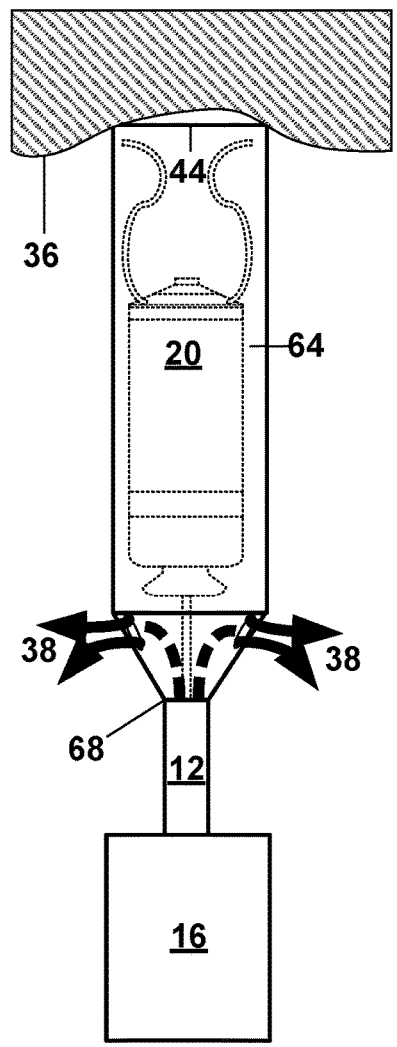
FIG. 10A
FIG. 10B
FIG. 10C

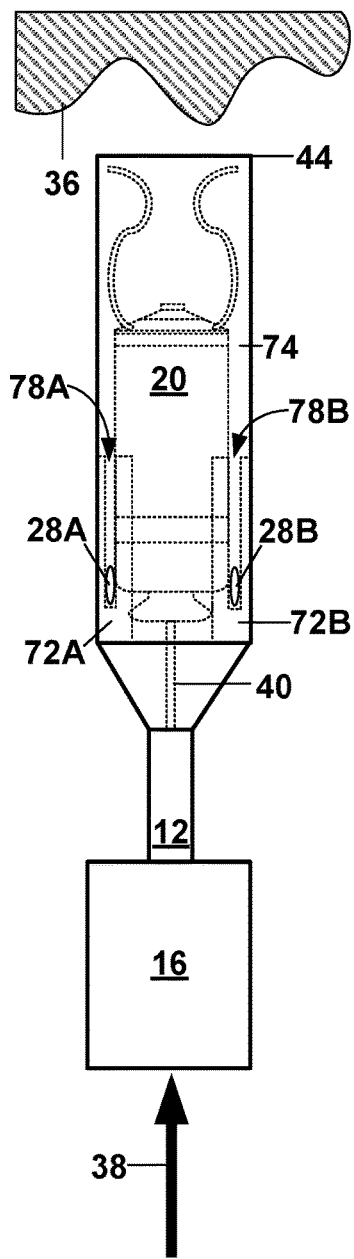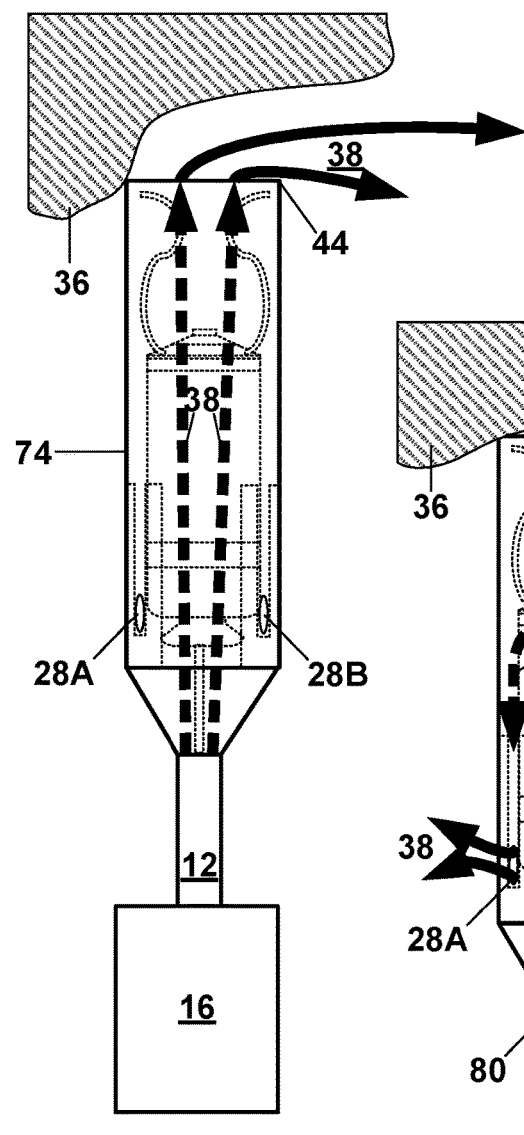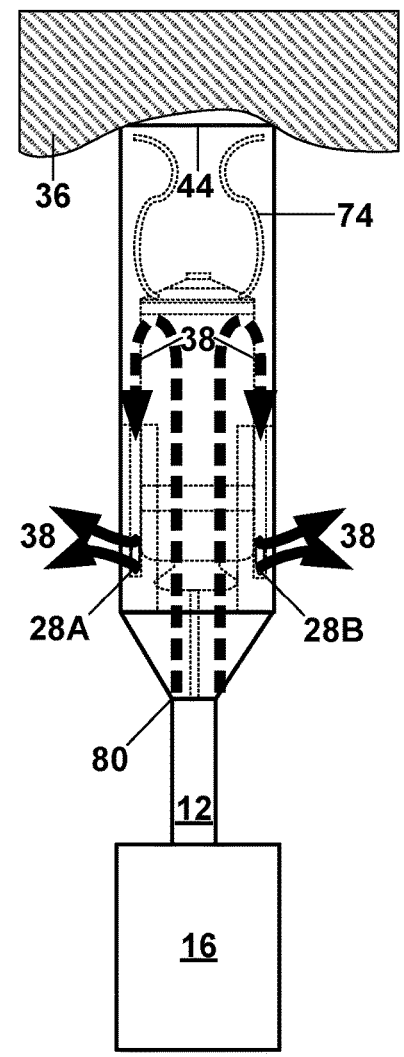
FIG. 12A
FIG. 12B
FIG. 12C

MEDICAL DEVICE DELIVERY SYSTEM WITH INTERNAL RIBS AND VENTS

This application claims the benefit of U.S. Provisional Patent Application No. 62/879,715, filed Jul. 29, 2019, the entire content being incorporated herein by reference.

TECHNICAL FIELD

This disclosure relates generally to medical devices, and, more particularly, to systems for delivering medical devices.

BACKGROUND

Some types of medical devices, such as cardiac pacemakers or implantable cardiac defibrillator systems, may be used to provide cardiac sensing and therapy for a patient via one or more electrodes. Some IMDs include an implantable pulse generator that includes a housing that encloses electronic components, which may be configured to be implanted subcutaneously in the chest of the patient or within a chamber of a heart of the patient, as examples. IMDs having a pulse generator that is configured to be implanted within a chamber of the heart may be referred to as an intracardiac device or a leadless implantable medical device. A delivery catheter may be used to deliver an intracardiac device transvenously to an implant site within a heart of a patient and release the device after the device has been fixed at the implant site. The delivery catheter then may be withdrawn from the patient.

SUMMARY

In general, this disclosure is directed to devices and systems for delivering an implantable medical device (IMD) within a vasculature of a patient. In some examples, a delivery device includes a cup configured to retain an IMD, the cup defining one or more internal ribs configured to secure the IMD within the cup. In some examples, the cup additionally or alternatively defines one or more vent holes and channels to allow the passage of fluids into and/or out of cup.

In one example, an implantable medical device delivery system comprises an elongate shaft extending from a proximal end of the elongate shaft to a distal end of the elongate shaft, the elongate shaft configured to extend through a vasculature of a patient; and a device cup attached to the distal end of the elongate shaft, the device cup comprising a cylindrical body configured to receive an implantable medical device, wherein the cylindrical body extends from a proximal end of the cylindrical body to a distal end of the cylindrical body, and wherein the cylindrical body comprises: an interior surface; an exterior surface; a distal opening at the distal end of the cylindrical body, the distal opening configured for passage of the implantable medical device; and at least one internal rib extending inwardly from the interior surface, the rib configured to contact the implantable medical device to frictionally retain the implantable medical device within the device cup.

Another example is a method for using a medical device delivery system. The system comprises an elongate shaft comprising a proximal end and a distal end; and a device cup attached to the distal end of the elongate shaft, the device cup comprising a cylindrical body configured to receive an implantable medical device, the cylindrical body comprising at least one vent hole disposed proximally of a distal end of the device cup. The method comprises introducing the distal end of the elongate shaft into a vasculature of a patient toward a tissue implant site; distally injecting a radioactive dye through the elongate shaft; observing the radioactive dye exiting at least one vent hole; and implanting an implantable medical device at the tissue implant site based on the observation of the radioactive dye exiting the at least one vent hole.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIGS. 10A-10C are plan views of the example device cup of FIG. 9, illustrating an example technique for using the cup in accordance with some examples of this disclosure.

FIGS. 12A-12C are plan views of the example device cup of FIGS. 11A-11E, illustrating an example technique for using the cup in accordance with some examples of this disclosure.

DETAILED DESCRIPTION

Figure 1:
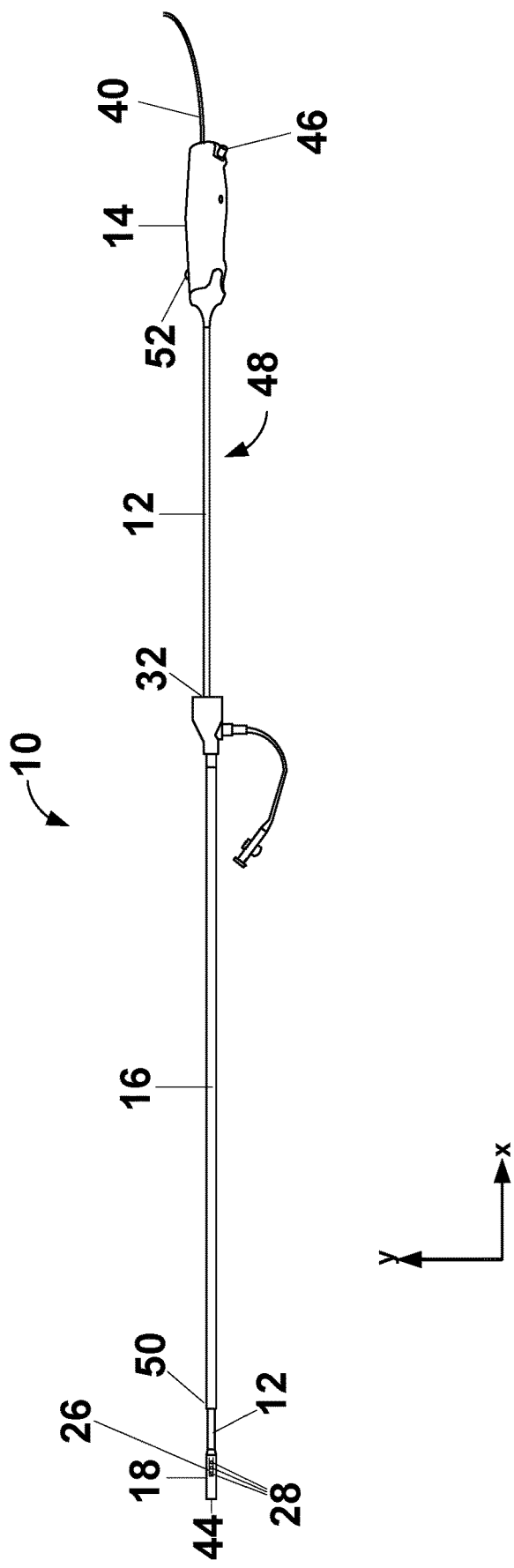
FIG. 1 is a side view illustrating a system for delivering an implantable medical device (IMD) within a vasculature of patient.

In general, this disclosure describes devices and systems for delivering an implantable medical device (IMD) within a vasculature or other anatomy of a patient. FIG. 1 is a conceptual drawing illustrating an example delivery system 10 for delivering an IMD (not shown in FIG. 1). System 10 includes inner member 48 and outer member 16. Although described herein in the context of delivering an IMD into the vasculature (e.g., the heart), the devices, systems, and techniques of this disclosure may be used to deliver an IMD to any anatomical location.

Outer member 16 (also referred to as an "introducer") is an elongated member defining an interior lumen. Outer member 16 includes proximal end 32 and distal end 50. Outer member 16 is configured to be inserted, such as by a physician, into a vasculature of a patient to provide a rigid channel (lumen) through which to insert a medical instrument, device, or other therapy.

Inner member 48 (also referred to as a "delivery catheter") is configured to be inserted through the lumen of outer member 16 to deliver a medical device within the vasculature. Inner member includes elongated shaft 12, handle 14, and device cup 18. Handle 14 is disposed at a proximal end of shaft 12, and may include one or more elements 52 (such as buttons, switches, etc.) configured to control the motion of the distal end of shaft 12. In some examples, handle 14 includes side port 46 for connection to a flushing assembly to enable delivery of fluid through a lumen defined by shaft 12 to device cup 18.

Device cup 18 is disposed at a distal end of shaft 12. Device cup 18 includes a hollow cylindrical body configured to house and support an IMD (e.g., IMD 20 described with respect to FIG. 3, below) while the IMD is being implanted within a vasculature of a patient. A distal end of a tether 40 may be attached to the IMD and extend through a lumen defined by shaft 12 of inner member 48. A physician may insert the distal end of inner member 48, including device cup 18, through the lumen of outer member 16, which is disposed within a vasculature of a patient. After device cup 18 has extended through distal end 50 of outer member 16 and reached an implant site within the patient, the physician may release the IMD from device cup 18, e.g., including releasing the IMD from tether 40, and withdrawing shaft 12 and cup 18 proximally through outer member 16.

Due to a variety of design considerations, the outer diameter of cup 18 may be only slightly less than an inner diameter of outer member 16. Withdrawal of cup 18 proximally through outer member 16 could cause proximal ejection of fluid (e.g., a bodily fluid of the patient) out of proximal end 32 of outer member 16, due to the movement of these closely matched diameters, which may create a piston-type or syringe-type suction, forcing fluid within outer member 16 out through proximal end 32.

In some examples in accordance with this disclosure, device cup 18 includes or defines one or more vent holes 28 configured to relieve fluid pressure within outer member 16, reducing or preventing such fluid ejection from proximal end 32. Vent holes 28 may relieve fluid pressure by providing an alternative path, e.g., through distal opening 44 of device cup 18, for fluid to exit the space between shaft 12 and outer member 16.

Figure 2:
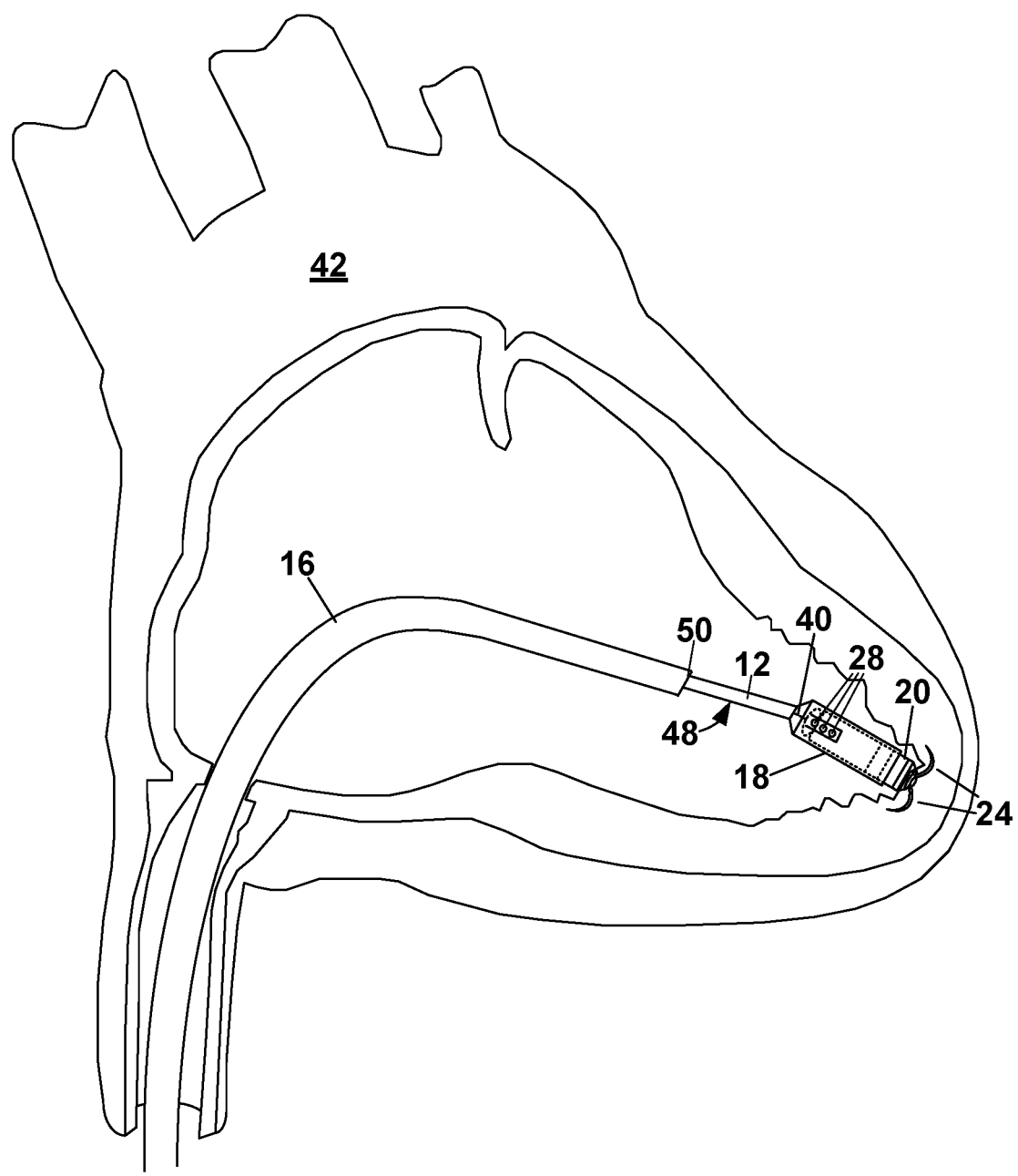
FIG. 2 is a conceptual drawing illustrating delivery of an example IMD from an example delivery system to an implant site within a patient.

FIG. 2 is a conceptual drawing illustrating delivery of an IMD 20 from medical device delivery system 10 to an implant site within a vasculature of a patient. The example of FIG. 2 illustrates IMD 20 having been delivered through outer member 16, which an operator has maneuvered up through the inferior vena cava IVC and the right atrium into the right ventricle of a patient's heart 42. IMD 20 and outer member 16 may be similar to the device and tool, respectively, described in the commonly assigned U.S. Pat. No. 9,526,522, assigned to Medtronic plc, of Dublin, Ireland.

In some instances, IMD 20 may be a pacemaker device having a housing that contains electronic components suitable for performing a variety of pacing functions. For example, IMD 20 may include an application-specific integrated circuit (ASIC), an electronic circuit, a processor (shared, dedicated, or group) and memory that execute one or more software or firmware programs, a combinational logic circuit, state machine, or other suitable components or combinations of components that provide pacing functionality. The particular form of software, hardware and/or firmware employed to implement the functionality disclosed herein will be determined primarily by the particular system architecture employed in the pacemaker and by the particular detection and therapy delivery methodologies employed by the pacemaker.

IMD 20 is shown fixed at an implant site by fixation members 24, but still secured by tether 40 within shaft 12 of inner member 48. Inner member 48 extends out from distal opening 50 of outer member 16. Shaft 12 is joined to device cup 18. Thus, the operator, via tether 40, is able to test the fixation of IMD 20 at the implant site, and/or remove IMD 20 from the implant site for repositioning at a more suitable site, if necessary. While IMD 20 is shown having fixation members 24 that include a plurality of tine structures, it should be understood that the techniques of this disclosure are not limited to any particular device fixation structure. For example, as described in greater detail herein, the disclosed devices may be used to rotate a screw-shaped fixation structure (helix) into tissue at an implant site.

Once satisfied with the implantation of IMD 20, the operator can separate IMD 20 from inner member 48, for example, actuating a mechanism at the proximal end of tether 40 to release the distal end of tether 40 from IMD 20, and then pulling proximally on handle 14 to withdraw an entirety of inner member 48 through outer member 16.

In some IMD delivery systems, after the operator has extended device cup 18 beyond distal end 50 of outer member 16 within the vasculature of a patient, one or more bodily fluids may accrue between shaft 12 and outer member 16. Absent vent holes 28, this fluid could be pulled or forced proximally by device cup 18 when the physician withdraws inner member 48 from outer member 16, and the fluid may eject toward the physician from proximal end 32 of outer member 16. However, in some examples in accordance with this disclosure, device cup 18 defines vent holes 28, configured to distally vent fluid toward the vasculature of the patient through the inside of device cup 18. Vent holes 28 may be configured, e.g., sized and shaped, to provide an alternative, and in some cases preferable path relative to distal end 32 of outer member 16 for the bodily fluid to exit the space between shaft 12 and outer member 16 at distal end 50 of outer member 16.

Figure 3:
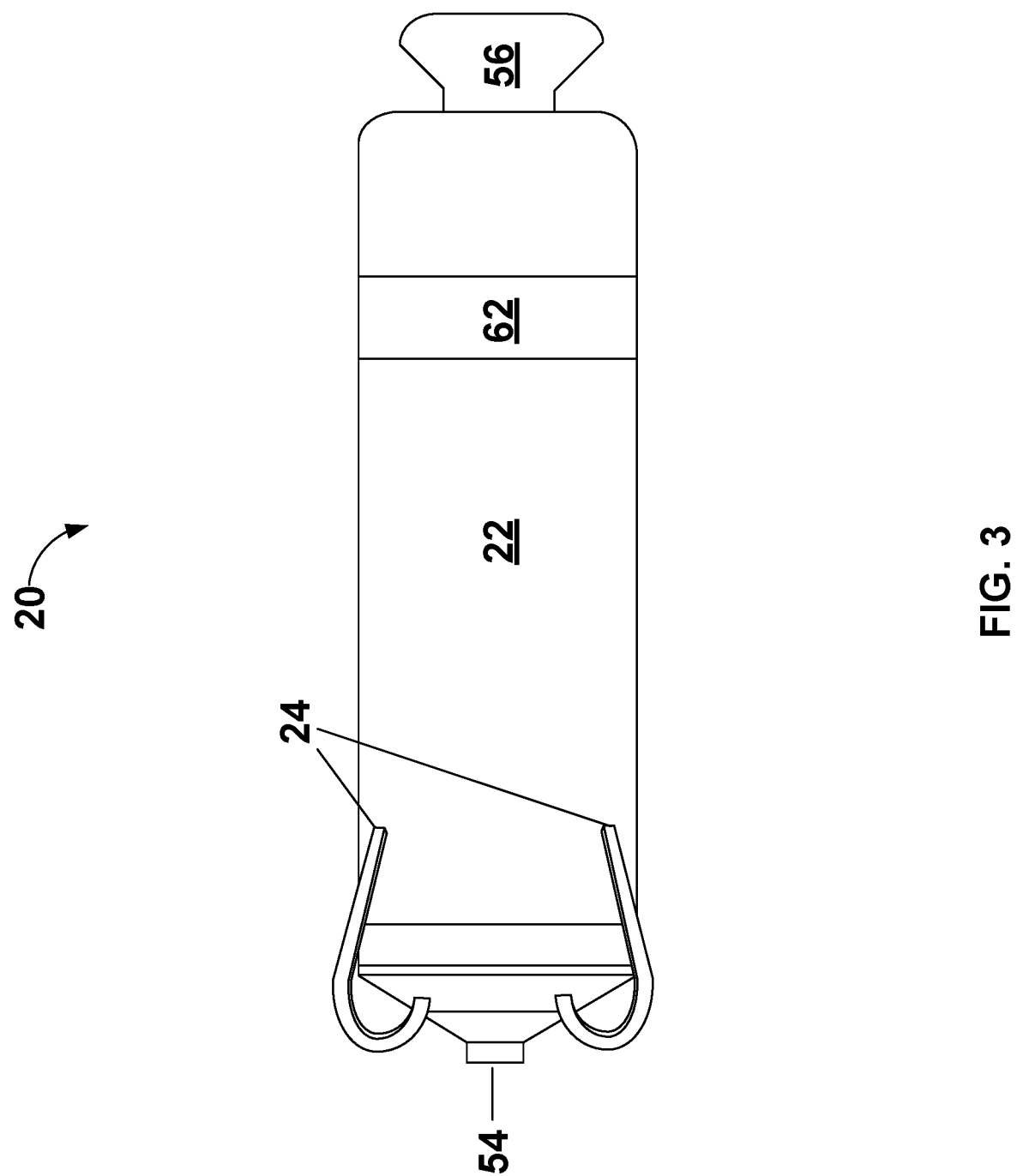
FIG. 3 is a plan view of an example IMD in accordance with some techniques of this disclosure.

FIG. 3 is a plan view of an example configuration of IMD 20. FIG. 3 illustrates IMD 20 including a housing 22. In some examples, housing 22 may be hermetically sealed. In some examples, an electronic controller (not shown), such as a pulse generator and an associated power supply, may be contained within housing 22. Features of example device cups, such as device cup 18, and their interaction with IMD 20 within the device cup, are described with respect to FIGS. 4-13.

IMD 20 includes an electrode 54 and fixation members 24. Electrode 54 may be electrically coupled to the controller via a hermetically sealed feedthrough assembly (not shown). Housing 22 may be formed from a biocompatible and biostable metal such as, for example, titanium, and overlaid with an insulative layer such as medical grade polyurethane, parylene, or silicone. In some examples, IMD 20 may include another electrode 62, for example, formed by removing a portion of the insulative layer to expose the metallic surface of housing 22. Electrode 62 may function in conjunction with electrode 54 for bipolar pacing and sensing, when fixation members 24 secure electrode 54 in intimate tissue contact at a target implant site. FIG. 3 further illustrates IMD 20 including an optional attachment structure 56 joined to housing 22. Tether attachment structure 56 may be configured for attachment to tether 40 (FIGS. 1 and 2) and snaring, for example, by a retrieval member (not shown).

With further reference to FIG. 3, device fixation members 24 are spaced apart from one another around a perimeter of device housing 22, wherein fixation members 24 are configured to fix device 20 to tissue at an implant site. Although only two fixation members 24 are illustrated in FIG. 3, IMD 20 may include four, as many as eight, or more than eight fixation members 24. According to one example, fixation members 24 are integrally formed with one another, having been cut from nickel titanium alloy tubing or other biocompatible tubing. After cutting the nickel titanium alloy tubing, members 24 may be shaped by bending and holding members 24 in the illustrated curvature while undergoing heat treatment. Fixation members 24 may be mounted to the distal end of device housing 22, for example, in a manner similar to that described for a fixation component 102 in U.S. Pat. No. 10,112,045, the description of which is hereby incorporated by reference in its entirety. The super-elastic nature of nickel titanium alloy allows fixation members 24 to elastically deform between a relaxed condition and an extended condition, in which a free end of each fixation member 24 extends distally away from device housing 22.

Figure 4:
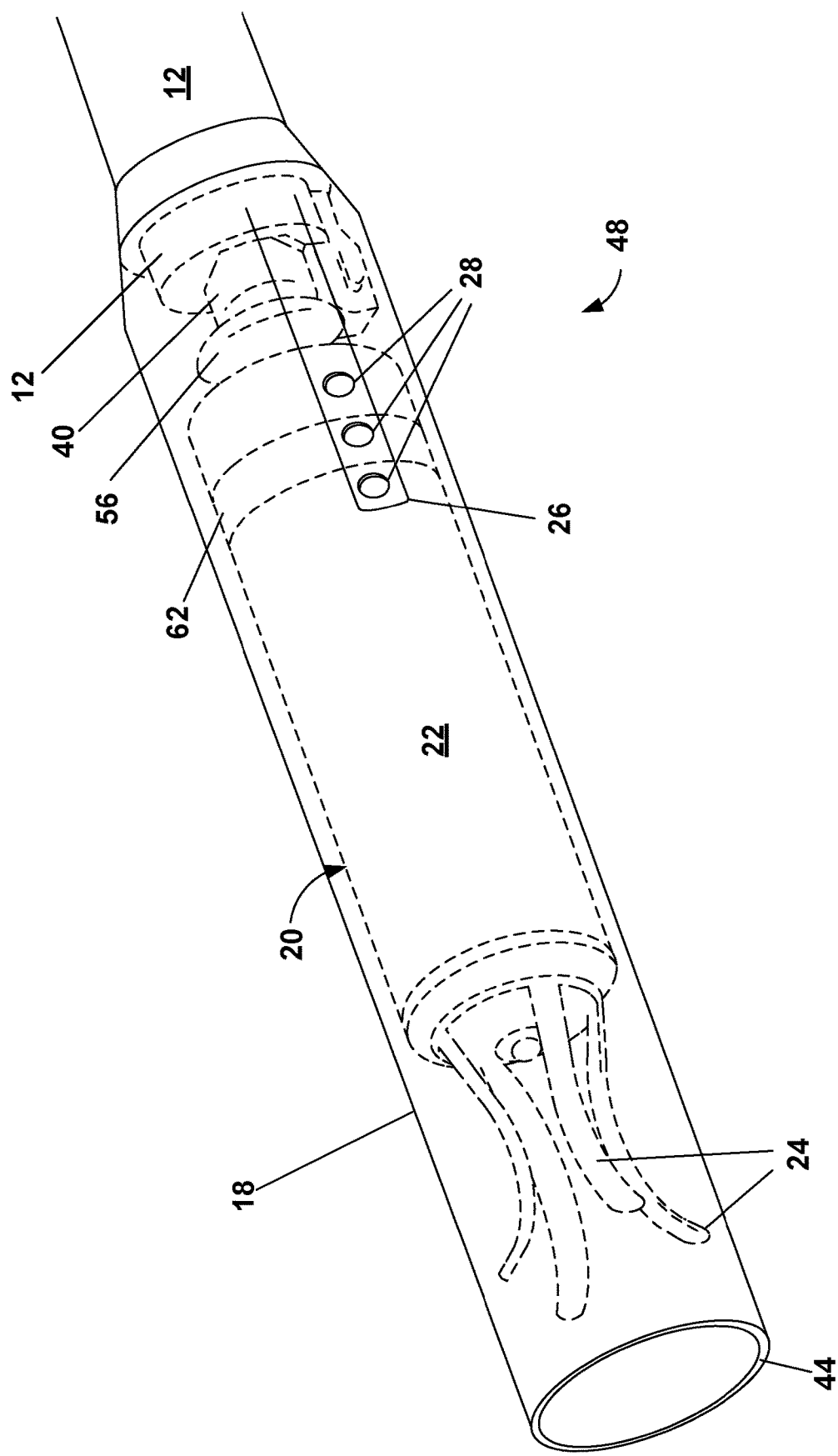
FIG. 4 is a perspective view of a cup containing an IMD according to some techniques of this disclosure.

FIG. 4 is a transparent perspective view of an example configuration of device cup 18 of FIGS. 1 and 2 containing IMD 20 of FIGS. 2 and 3. Device cup 18 includes a hollow cylindrical member attached to a distal end of shaft 12 of inner member 48. In some examples, device cup 18 may have an outer diameter of about 0.308 inches, an inner diameter of about 0.275 inches, and a thickness (the difference between the outer and inner diameters) of about 0.016 inches.

Device cup 18 is configured to house and support IMD 20. Inner member 48 may include an elongated tether 40 passing through an inner lumen of shaft 12. A distal end of tether 40 may be configured to removably connect to a distal end of IMD 20, such as to attachment structure 56.

As illustrated in FIG. 4, device cup 18 includes vent holes 28. A vent hole 28 may include an opening extending from the outer or exterior surface to the inner or interior surface of device cup 18, configured to vent fluid from the exterior surface to the interior surface, from the interior surface to the exterior surface, or both. In the example of FIG. 4, device cup 18 includes a plurality (in this example three) vent holes 28 distributed longitudinally along the cylindrical body of device cup 18. In other examples, device cup may include any number of one or more vent holes 28, which may be distributed in any manner on device cup, e.g., longitudinally and/or circumferentially. In some examples, such as the example illustrated by FIG. 4, vent holes 28 may be located nearer to a proximal end of device cup 18 than to a distal end, e.g., to avoid interaction with tines 24 of IMD 20 and/or to place one or more vent holes over electrode 62 of IMD 20.

As illustrated by FIG. 4, device cup 18 may also include one or more external channels 26. An external channel 26 may include an elongated depression into the outer surface of device cup 18, configured to direct fluid from an exterior surface of device cup 18 down into vent holes 28. External channels 26 may extend from at or near a proximal end of device cup 18 to a location of vent holes 28 to provide a preferential path for fluid that has accrued between shaft 12 and outer member 16 proximal of device cup 18 to flow to vent holes 28. As illustrated in FIG. 4, vent holes 28 may be located within external channels 26 and, in some cases, more near a distal end then a proximal end of the channel.

Although not illustrated in FIG. 4, device cup 18 may additionally or alternatively include one or more internal channels 78 (FIG. 11). Internal channels 78 may include a defined fluid pathway along the inner surface of device cup 18, configured to direct fluid from an interior surface of device cup 18 up into vent holes 28. Direction of fluid from the interior to the exterior of device cup 18, e.g., radioactive dye to visually determine alignment of distal opening 44 of cup 18 with tissue, is described in greater detail below. The size, shape, and number of vent holes 28, external channels 26, and internal channels 78 (such as the diameter of vent holes 28, and length, width, and depth of channels 26 and 78) may be configured based on characteristics of fluids with which they will interact, desired degrees of fluid flow, and other conditions of use of system 10.

Figure 6:
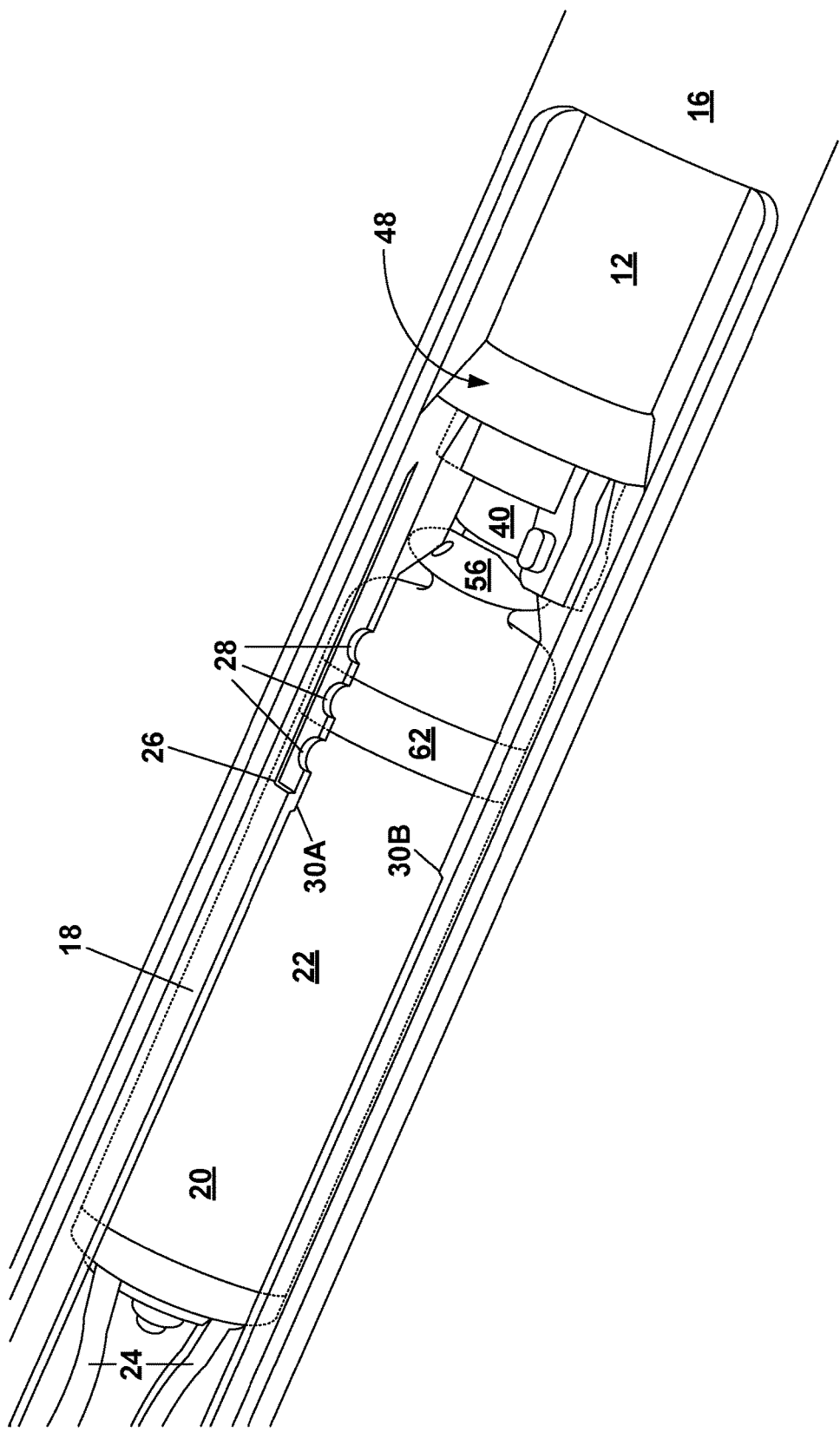
FIG. 6 is a perspective view of the cup and IMD of FIGS. 4 and 5 within an example introducer device with portions of the introducer device and cup omitted.
Figure 7:
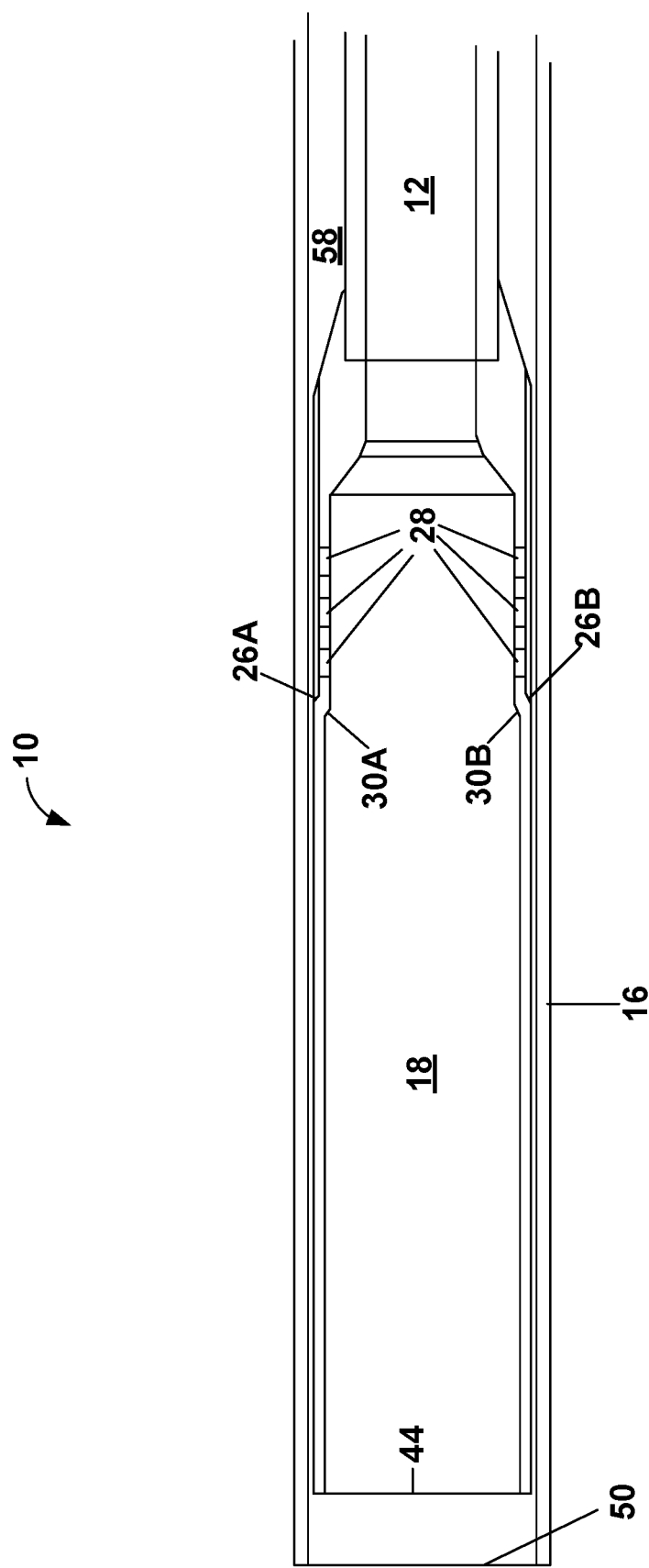
FIG. 7 is a cross-sectional side view of the IMD delivery system depicted in FIG. 1.

Although not illustrated in FIG. 4, device cup 18 may include one or more internal ribs 30 (FIGS. 6 and 7). An internal rib 30 may include an elongated protuberance extending inwardly from the inner surface of device cup 18. In some examples, internal ribs 30 may be configured to define internal channels such as internal channel 78. A long dimension of external channels 26, internal channels 78, and internal ribs 30 may be, but is not necessarily, in the direction of the longitudinal axis of device cup 18. In some examples, internal ribs 30 may contact the outer surface 22 of IMD 20, creating more friction between device cup 18 and IMD 20, providing for better control over the IMD 20 (e.g., holding IMD 20 more firmly in place within device cup 18). In this manner, internal ribs 30 may contact outer surface 22 of IMD 20 to frictionally retain IMD 20 within device cup 18.

In examples in accordance with this disclosure, various numbers, combinations, configurations and arrangements of external channels 26, internal channels 78, internal ribs 30, and/or vent holes 28 may provide respective advantages to a physician or other operator of system 10 (FIG. 1). As discussed above, such advantages may include, but are not limited to, improved control over (e.g., retention of) IMD 20, relief of fluid pressure, and/or visual alignment of system 10 with respect to the vasculature and target implant tissue of a patient.

Figure 5:
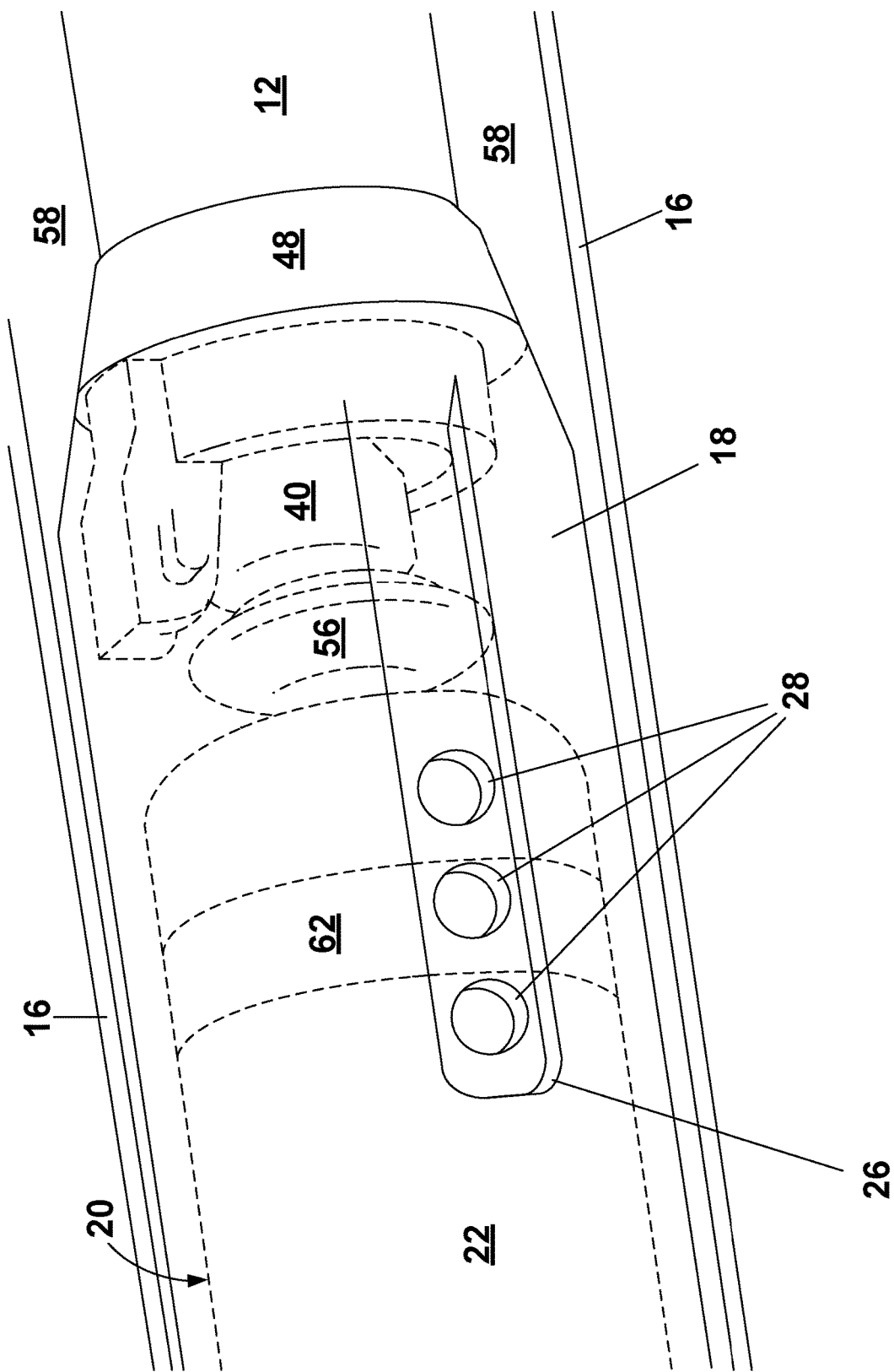
FIG. 5 is a close-up perspective view of the cup and IMD depicted in FIG. 4.

FIG. 5 is a close-up perspective view of device cup 18 and IMD 20 within outer member 16. In the example depicted in FIG. 5, device cup 18 defines external channel 26 and three vent holes 28. External channel 26 includes an elongated depression into the exterior surface of device cup 18 that does not extend through the surface. External channel 26 may extend distally from a proximal end of device cup 18. In some examples, device cup 18 may define multiple external channels 26 arranged circumferentially around the cylindrical body of device cup 18.

Device cup 18 defines vent holes 28 within external channel 26. Vent holes 28 include one or more openings extending from the exterior surface of device cup 18 to the interior surface of device cup 18, i.e., through device cup 18. In some examples, vent holes 28 may be substantially round, and have a diameter of about 0.025-0.050 inches. For example, vent holes 28 may have a diameter of 0.036 inches. In other examples, vent holes 28 may have other shapes, such as rectangular or elliptical shapes. In some examples, vent holes 28 may be elongated and rounded "slots," e.g., shaped like a hockey rink. In some examples in which vent holes 28 have an elongated shape, e.g., in which a size of the hole along one axis is greater than the size along another, orthogonal axis, the axis having the larger size may be oriented substantially parallel to the longitudinal axis defined by cup 18. Elongated vent holes 28 may increase the likelihood that electrode 62 of IMD 22 is exposed to blood to facilitate electrical measurements using the electrode while the IMD is within the cup, e.g., because IMD 22 may move longitudinally within cup 18.

Vent holes 28 may initially be "plugged" by IMD 20 while IMD 20 is housed within device cup 18. After a physician or other operator has released IMD 20 into the vasculature of a patient, system 10 may accrue fluids between shaft 12 and outer member 16, for example, in region 58. Absent external channel 26 and vent holes 28, this fluid may be pulled proximally or forced by device cup 18 when the physician withdraws inner member 48 from outer member 16, and the fluid may eject toward the physician. Because device cup 18 defines external channel 26 and vent holes 28, however, this fluid will instead be forced into external channel 26 and into vent holes 28. The fluid may then exit distally (e.g., toward the internal vasculature of the patient through the inside of device cup 18).

In some examples, vent holes 28 may be arranged circumferentially around the cylindrical body of device cup 18. In some examples, like the example depicted in FIG. 5, vent holes 28 may additionally or alternatively be arranged longitudinally along device cup 18. In some examples, vent holes 28 may be nearer to a proximal end of device cup 18 than to distal end 44 (FIG. 7).

In some examples, one or more of vent holes 28 may be disposed near or directly over ring electrode 62 of IMD 20. In these examples, vent hole 28 allows bodily fluid within patient to contact ring electrode 62. When an electrically conductive fluid contacts both electrode 54 and ring electrode 62 of IMD 20, a circuit may be completed, allowing a user to activate IMD 20 while it is still housed within device cup 18. Some examples may be configured with internal ribs, e.g., internal ribs 30, that allow fluid to reach ring electrode 62 despite vent hole 28 not being directly overtop the electrode.

In some examples, a user may determine whether cup 18 and IMD 20 are properly positioned relative to the heart tissue based on an impedance or other electrical parameter of a signal delivered via an electrical path including electrodes 54 and 62, or other electrodes included in delivery system 10. In some examples, relatively higher impedance may be indicative of cup 18 being positioned flush against, and with adequate depth in, tissue of the heart, which may be desirable for proper fixation. Some examples may employ any of the techniques for testing the spatial relationship of a cup and/or IMD to tissue described in U.S. patent application Ser. No. 16/146,391, filed Sep. 28, 2018 by Medtronic, Inc., and titled "Impedance-Based Verification for Delivery of Implantable Medical Devices," which is incorporated herein by reference in its entirety.

FIG. 6 is a perspective view of the device cup 18 and IMD 20 with portions of outer member 16 and device cup 18 removed to illustrate an example longitudinal, cross-sectional profile of device cup 18. In the example depicted in FIG. 6, device cup 18 defines at least two internal ribs 30A and 30B (collectively, internal ribs 30), evenly spaced around the inner circumference of device cup 18. For example, device cup 18 may define two ribs 30 spaced 180 degrees apart from each other. In other examples, device cup 18 may define three internal ribs 30, spaced 120 degrees apart from each other around the inner circumference of device cup 18. Internal ribs 30 include elongated protuberances extending inwardly from the inner surface of device cup 18. For example, internal ribs 30 may extend inwardly (e.g., radially) from the inner surface of device cup 18 toward the central axis of device cup 18. Internal ribs 30 may extend inwardly, for example, about 0.075 inches.

In some examples, internal ribs 30 may contact the outer surface 22 of IMD 20, creating more friction between device cup 18 and IMD 20, providing for better control over the IMD 20 (e.g., holding IMD 20 more firmly in place within device cup 18). In some examples, device cup 18 may define more than two internal ribs 30 distributed circumferentially around the interior surface of device cup 18. For example, device cup 18 may define three internal ribs 30, each internal rib spaced 120 degrees apart from the other two. In this example configuration, the flexible material of device cup 18 may slightly deform from having a perfectly circular cross-section to a slightly triangular cross-section when IMD 20 is inserted and gripped by the internal ribs at their three locations. In some examples, device cup 18 may be biased, e.g., like a spring, to its undeformed condition, providing a force exerted on IMD 20 by internal ribs 30 to hold IMD 20 within device cup 18.

In some examples, an internal rib (such as internal rib 30A) may be formed along the opposite (inner) surface of device cup 18 from a corresponding external channel (such as external channel 26), such that the thickness of the wall of device cup 18 is uniform throughout device cup 18. In other examples, an internal rib (such as internal rib 30B), does not have a corresponding external channel, (e.g., the rib is disposed on an opposite surface of a uniform exterior surface of device cup 18), such that the wall of device cup 18 is thicker along internal rib 30B compared to the rest of the cup. In these examples, internal rib 30B may be configured to hold and retain IMD 20, but not necessarily to vent fluid.

Figure 8:
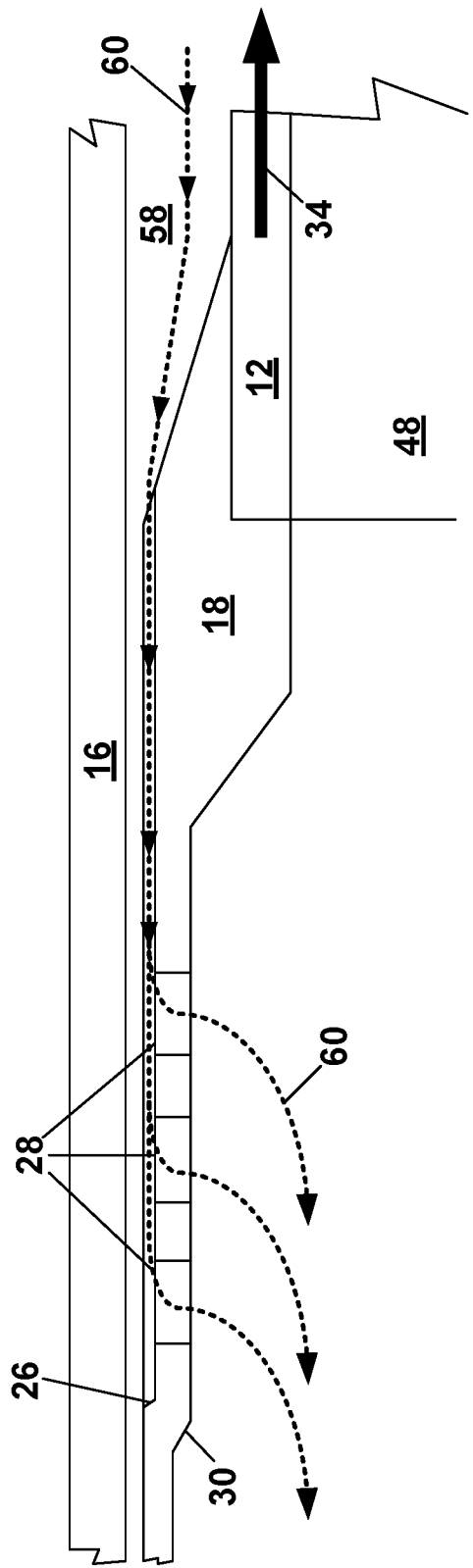
FIG. 8 is another cross-sectional side view of the system depicted in FIG. 7, illustrating an example flow of fluid through vents defined by the cup.

FIG. 7 is a cross-sectional side view of IMD delivery system 10. In the example depicted in FIG. 7, device cup 18 defines a pair of external channels 26A and 26B (collectively, external channels 26). Each of external channels 26 corresponds to a respective internal rib 30A and 30B defined by the inner surface of device cup 18. Further, each pair of exterior channels 26 and interior ribs 30 defines three vent holes 28. As illustrated in FIG. 8, when a physician proximally withdraws inner member 48 (indicated by thick black arrow 34) through outer member 16, fluid 60 will be forced distally (i.e., the direction opposite to arrow 34) from region 58, through vent holes 28, into the interior region of device cup 18 previously occupied by IMD 20, and outward through distal end 44 of device cup 18 (FIG. 7).

In addition to directing fluid during withdrawal of inner member 48 through an outer member 16 after implantation of an IMD, vent holes 28 may be used to indicate an alignment of an IMD delivery system and, more particularly, a device cup, with respect to a target tissue of a patient prior to implantation of the IMD. FIGS. 9 and 10A-C illustrate another example IMD delivery system 60, which may be similar to IMD delivery system 10 (FIGS. 1-8) except as otherwise noted. IMD delivery system 60 includes an example arrangement of vent holes 28, which may allow a physician to determine an alignment of IMD delivery system 60 with respect to a tissue of a patient at an implant site.

For example, a physician may inject a radioactive dye into IMD delivery system 60. Depending on the placement of system 60 with respect to the patient's vasculature, the radioactive dye may exit system 60 either through distal end 44 of device cup 64 (indicating incorrect placement of system 60) or through vent holes 28 (indicating correct placement of system 10), which may be located nearer a proximal end of device cup 64 than to distal end 44. The location at which dye exits device cup 64 may be highly visually apparent on a fluoroscopy or other image of the tissue implantation site, indicating the alignment of IMD delivery system 60.

Figure 9:
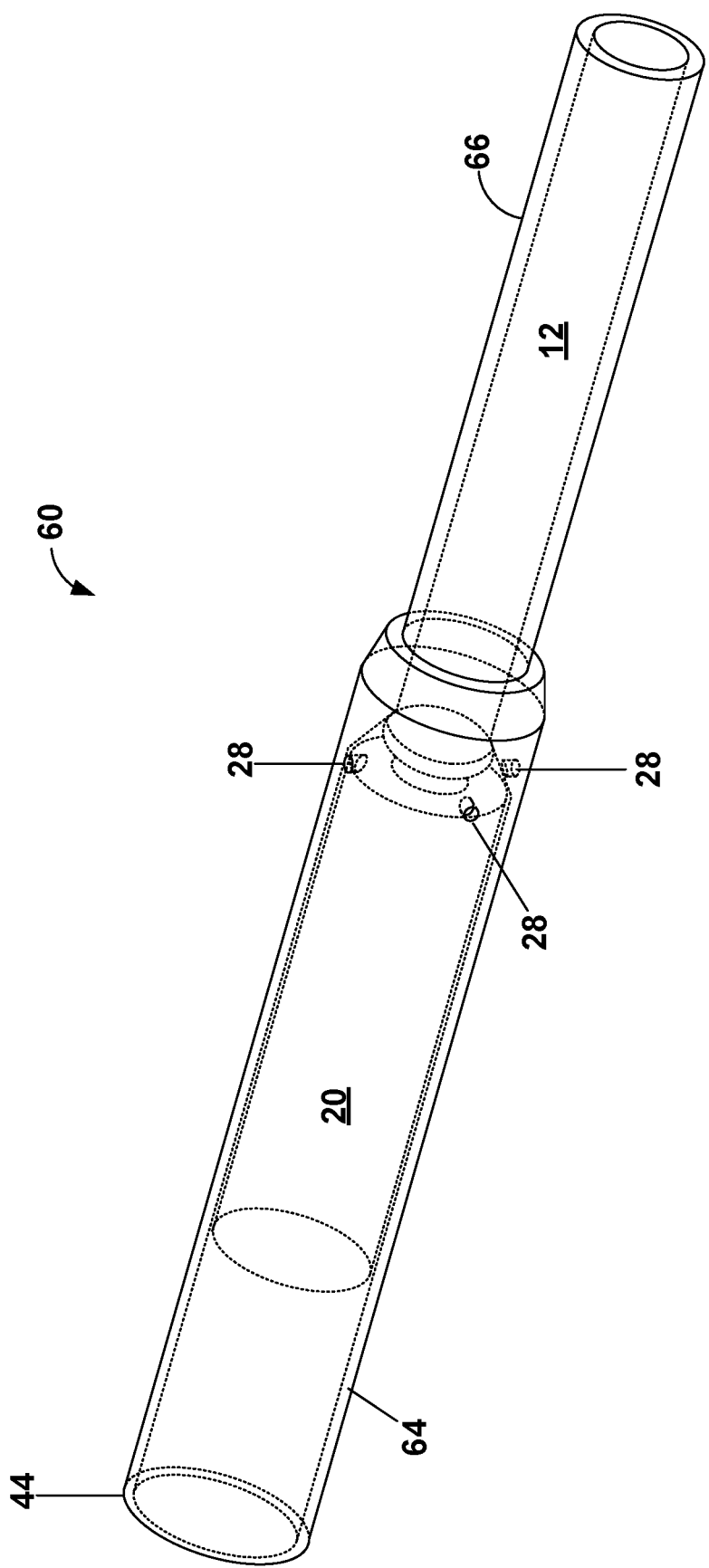
FIG. 9 is a perspective view of another example system for delivering an IMD within a vasculature of a patient, in accordance with some examples of this disclosure.

FIG. 9 is a perspective view of system 60 including a device cup 64 attached to a distal end of elongated shaft 12 of an inner member 66, in accordance with some examples of this disclosure. In the example depicted in FIG. 9, device cup 64 defines three vent holes 28, however it is to be understood that device cup 64 may define any number of vent holes. Although not illustrated in FIGS. 9-10C, device cup 64 may include one or more internal ribs and/or internal channels defining a pathway for the flow of radioactive dye 38 (FIG. 10B). In the example of FIG. 9, vent holes 28 are not configured to vent a patient's fluid into device cup 64 during withdrawal of device cup 64 through outer member 16, since the holes will be "plugged" by the inner surface of outer member 16 and there are no corresponding external channels to direct fluid into the holes. However, if vent holes 28 are disposed along the narrower circumference of the conical proximal section of device cup 64 (as shown in FIGS. 10A-10C), then vent holes 28 will not be plugged by outer member 16, and an external channel is not needed for a patient's fluid to enter device cup 64 through vent holes 28.

FIGS. 10A-10C depict the example device cup 64 of FIG. 9 in conjunction with patient tissue 36 at an implant site, e.g., during a procedure to implant IMD 20. As shown in FIG. 10A, a physician or other operator may navigate the distal end 44 of device cup 64 toward a tissue implant site 36 within a vasculature of a patient. Once the physician has aligned distal end 44 with tissue 36, the physician may distally inject radioactive dye 38 through the inner lumen of shaft 12.

As depicted in FIG. 10B, in some scenarios, the physician may not have adequately aligned the distal end 44 of device cup 64 with the tissue 36. For example, as shown in FIG. 10B, distal end 44 may be disposed at an angle to tissue 36. In these examples, a greater portion of radioactive dye 38 may escape device cup 18 from the gap formed between distal end 44 and tissue 36. The resulting plume of radioactive dye 38 near the implant site may appear vividly on fluoroscopy imagery of the surrounding region, informing the physician or operator that device cup 64 is misaligned. In this configuration, a small amount of radioactive dye 38 may also escape through vent holes 28.

As depicted in FIG. 10C, in some scenarios, the physician may have successfully aligned distal end 44 of device cup 64 with tissue 36 at an implant site for IMD 20. For example, the entire distal end 44 may be covered or capped by tissue 36. In these examples, a greater portion of radioactive dye 38 may escape device cup 64 through vent holes 28 than when distal end 44 was misaligned with tissue 36. The resulting plume of radioactive dye 38, disposed a notable distance proximally from implant site 36, may appear vividly on fluoroscope imagery of the surrounding region, informing the physician or operator that device cup 64 is correctly aligned, and IMD 20 may be implanted at site 36. In some examples, the portion of dye 38 that exits vent holes 28 may be increased in response to adequate pressure of distal end 44 against tissue 36 and "tenting" of tissue 36.

Values of a variety of parameters may be selected to facilitate the differential flow of dye 38 through vent holes 28 depending on the degree of contact of distal end 44 with tissue 36. In some examples, the combined diameters of vent holes 28 may be selected to be less than a difference between a diameter of cup 64 and IMD 20, e.g., a certain amount, fraction, or percentage less than the diameter difference. The diameters of each of vent holes 28 may be selected based on the density of dye 38. The shape of vent holes 28 and radial positions of vent holes 28 may be selected to achieve a desired shape of the plume of dye 38.

A position of vent holes 28 along a longitudinal axis of device cup 64 may be selected to be closer to the proximal end 68 of cup 64 than distal end 44 to avoid interference of vent holes 28 with the fixation members of IMD 20 and to allow dye 38 exiting vent holes 28 to be distinguished from dye 38 exiting distal end 44 of device cup 64. On the other hand, shorter longitudinal distances between distal end 44 and vent holes 28 may facilitate one or more of vent holes 28 being intentionally covered in response to device cup 64 applying pressure greater than and/or achieving tenting than some predefined degree of pressure and/or tenting.

Figure 11A:
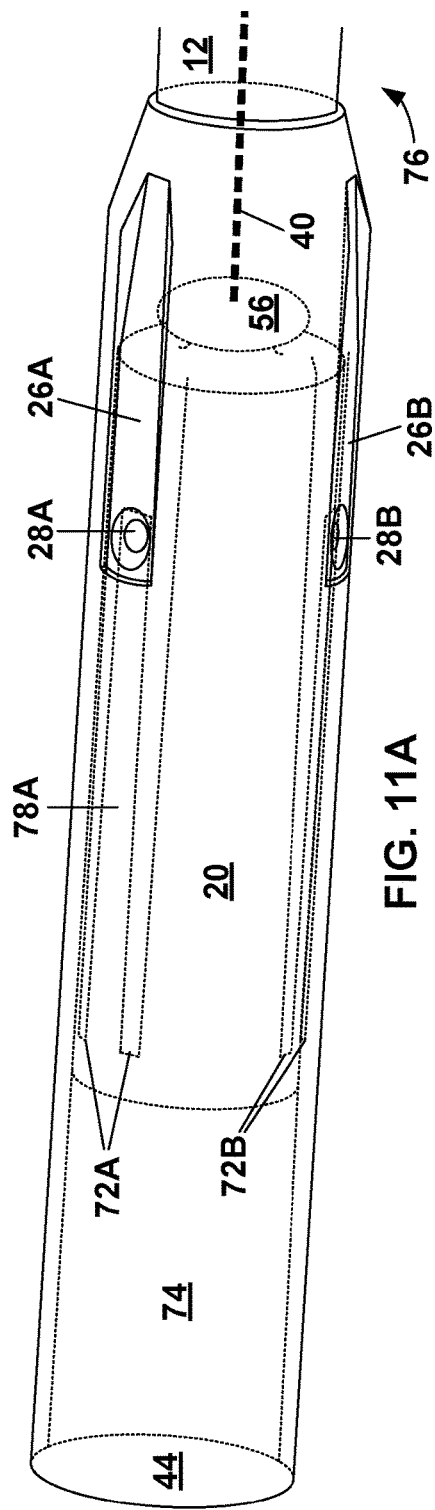
FIGS. 11A-11E are perspective views of another example system for delivering an IMD within a vasculature of a patient, in accordance with some examples of this disclosure.
Figure 11B:
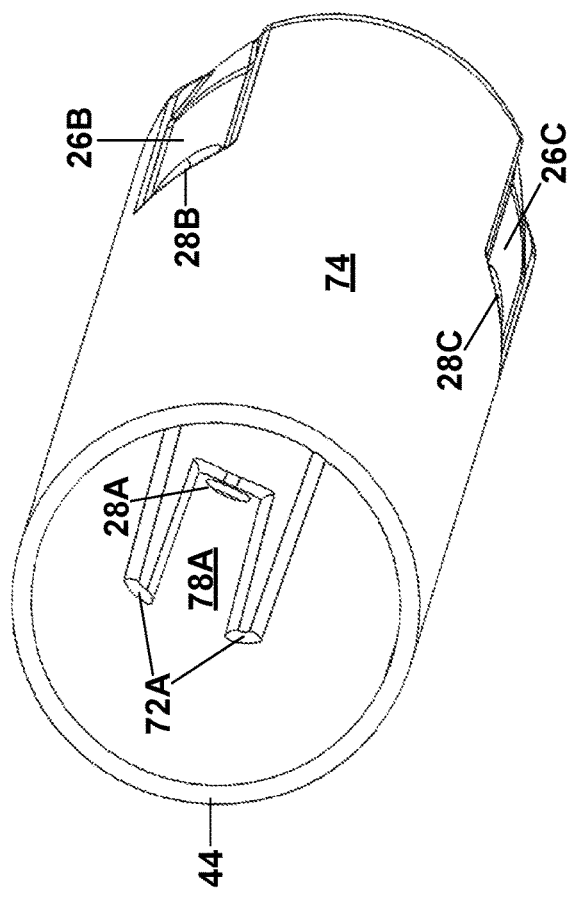
Figure 11C:
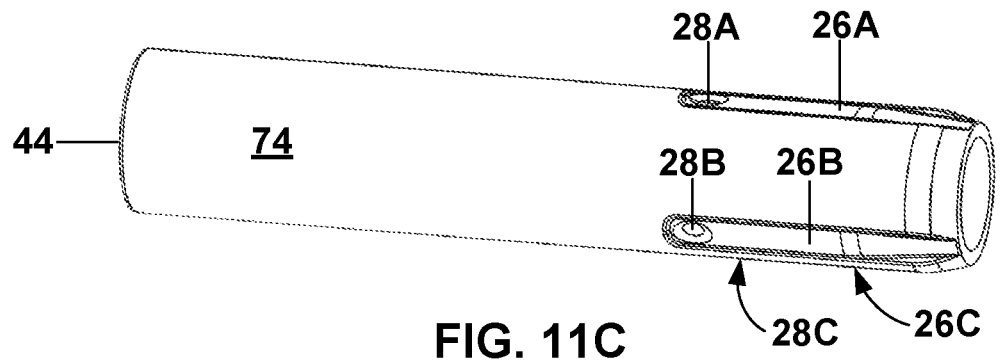
Figure 11D:
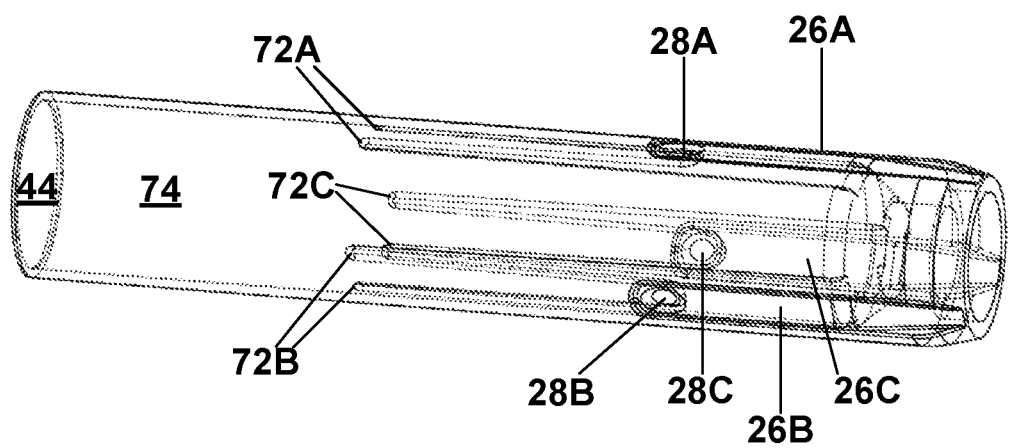
Figure 11E:
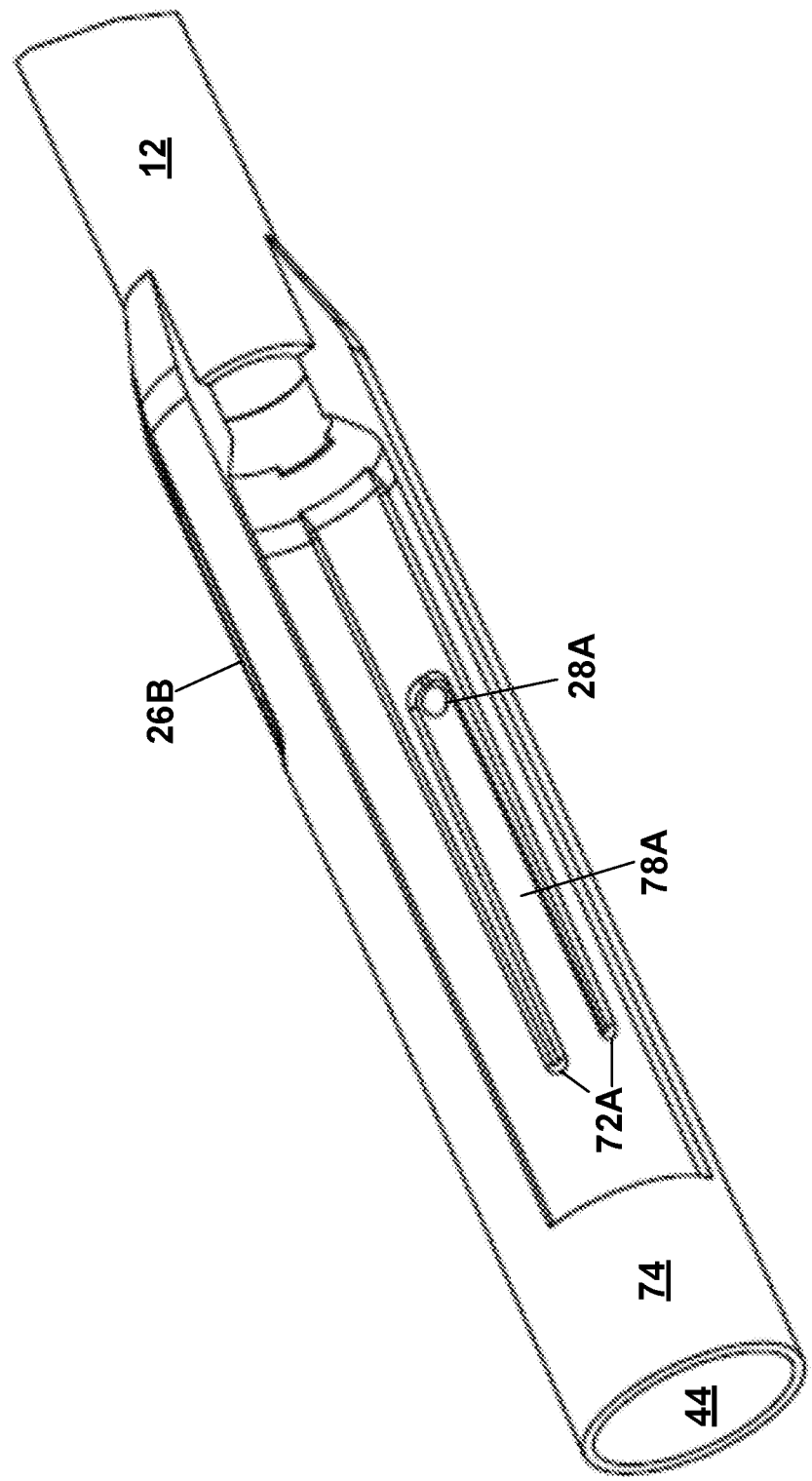

FIGS. 11A-11E depict another example device cup 74 attached to a distal end of elongated shaft 12 of an inner member 76, in accordance with some examples of this disclosure. FIG. 11A is a transparent perspective view of device cup 74 containing IMD 20. FIG. 11B is an opaque perspective view of the interior surface of device cup 74 with IMD 20 removed. FIG. 11C is an opaque perspective view of the exterior surface of device cup 74. FIG. 11D is a transparent perspective view of device cup 74 with IMD 20 removed. FIG. 11E is an opaque perspective view of device cup 74 with a portion of cup 74 removed.

As depicted in FIGS. 11A-11E, the exterior surface of device cup 74 defines three external channels 26A-26C (collectively, external channels 26). Each external channel 26 contains one vent hole 28A-28C, respectively (collectively, vent holes 28). However, it is to be understood that device cup 74 may define any number of external channels and, each external channel 26 may contain any number or shape of vent holes 28. The example device cup 74 depicted in FIGS. 11A-11E also defines three internal ribs 72A-72C (collectively, internal ribs 72), each internal rib 72 corresponding to one external channel 26 and one vent hole 28, respectively. These internal ribs 72 may contact and retain IMD 20, spacing the outer circumference of IMD 20 away from the inner circumference of device cup 74, and allowing vent holes 28 to vent a patient's fluid regardless of whether IMD 20 is present within device cup 74.

In the example configuration depicted in FIGS. 11A-11E, each internal rib 72 includes a distal bifurcated structure defining a pair of parallel elongated extensions, shaped similar to the dual prongs of a tuning fork.

Each of these dual extensions further define respective sides of internal channel 78A-78C, respectively (collectively, internal channels 78). It is to be understood that, although internal channels 78 are referred to as "channels", unlike external channels 26, internal channels 78 may be flush or level with the corresponding surface of device cup 74, apart from the corresponding internal rib 72 that defines their borders.

In the examples depicted in FIGS. 11A-11E, internal ribs 72 are depicted as pairs of straight, parallel extensions. In other examples, internal ribs 72 may be formed to have a helical shape, such as by rotating device cup 74 during the molding process. As described further with respect to FIGS. 12A-12C below, internal channels 78 may improve the visual alignment of device cup 74 within a vasculature of a patient by directing a flow of radioactive dye away from or toward vent holes 28. The dimensions, shapes, and/or materials of internal ribs 72 and internal channels may be selected to facilitate a desired flow of dye. In some examples, porous media and/or valves may be used within channels 78 or otherwise within device cup 74 to facilitate a desired flow of dye. In some examples, porous media may be included within device cup 74 in addition to or instead of ribs/channels, and may be configured to provide a desired flow of dye or other fluids within the cup.

FIGS. 12A-12C depict the example device cup 74 of FIGS. 11A-11E. As shown in FIG. 12A, a physician or other operator may navigate the distal end 44 of device cup 74 toward a tissue implant site 36 within a vasculature of a patient. Once the physician has aligned distal end 44 with tissue 36, the physician may distally inject radioactive dye 38 through the inner lumen of shaft 12.

As depicted in FIG. 12B, in some scenarios, the physician may not have adequately aligned the distal end 44 of device cup 74 with the tissue 36. For example, as shown in FIG. 12B, distal end 44 may be disposed at an angle to tissue 36 (e.g., the longitudinal axis of device cup 74 is not disposed perpendicularly to tissue 36). In these examples, radioactive dye 38 will travel from shaft 12 toward distal end 44 of device cup 74. Radioactive dye 38 will be largely prevented from escaping through vent holes 28, because vent holes 28 are bordered on either side by the dual prongs of internal ribs 72 as well as by IMD 20, which may be in physical contact with internal ribs 72. Accordingly, a greater portion of radioactive dye 38 may escape device cup 74 from the gap formed between distal end 44 and tissue 36. The resulting plume of radioactive dye 38 near tissue implant site 36 may appear vividly on fluoroscopy imagery of the surrounding region, informing the physician or operator that device cup 74 is misaligned with the tissue.

As depicted in FIG. 12C, in some scenarios, the physician may have successfully aligned distal end 44 of device cup 74 with tissue 36 at an implant site for IMD 20. For example, the entire distal end 44 may be covered or capped by tissue 36. In these examples, radioactive dye 38 will travel distally from shaft 12 toward distal end 44, where it will be trapped by tissue 36, and be redirected down into internal channels 78 defined by the tuning-fork-shaped internal ribs 72, and out through vent holes 28. Accordingly, a greater portion of radioactive dye 38 may escape device cup 18 out through vent holes 28 than when distal end 44 was misaligned with tissue 36 (as in FIG. 12B). The resulting plume of radioactive dye 38, disposed a notable distance proximally from implant site 36, may appear vividly on fluoroscopy imagery of the surrounding region, informing the physician or operator that device cup 74 is correctly aligned with tissue 36, and IMD 20 may be implanted at tissue site 36. In some examples, the portion of dye 38 that exits vent holes 28 may also be increased in response to adequate pressure of distal end 44 against 36 and "tenting" of tissue 36.

Values of a variety of parameters may be selected to facilitate the differential flow of dye 38 through vent holes 28 depending on the degree of contact of distal end 44 with tissue 36. In some examples, the combined diameters of vent holes 28 may be selected to be less than the difference between a diameter of cup 74 and IMD 20, e.g., a certain amount, fraction, or percentage less than the diameter difference. The diameters of each of vent holes 28 may be selected based on the density of dye 38. The shape of vent holes 28 and radial positions of vent holes 28 may be selected to achieve a desired shape of the plume of dye 38.

A position of vent holes 28 along a longitudinal axis of device cup 74 may be selected to be closer to the proximal end 80 of cup 74 than distal end 44 to avoid interference of vent holes 28 with the fixation members 24 of IMD 20 and to allow dye 38 exiting vent holes 28 to be distinguished from dye 38 exiting distal end 44 of device cup 74. On the other hand, shorter longitudinal distances between distal end 44 and vent holes 28 may facilitate one or more of vent holes 28 being intentionally covered in response to device cup 74 applying pressure greater than and/or achieving tenting than some predefined degree of pressure and/or tenting.

Figure 13:
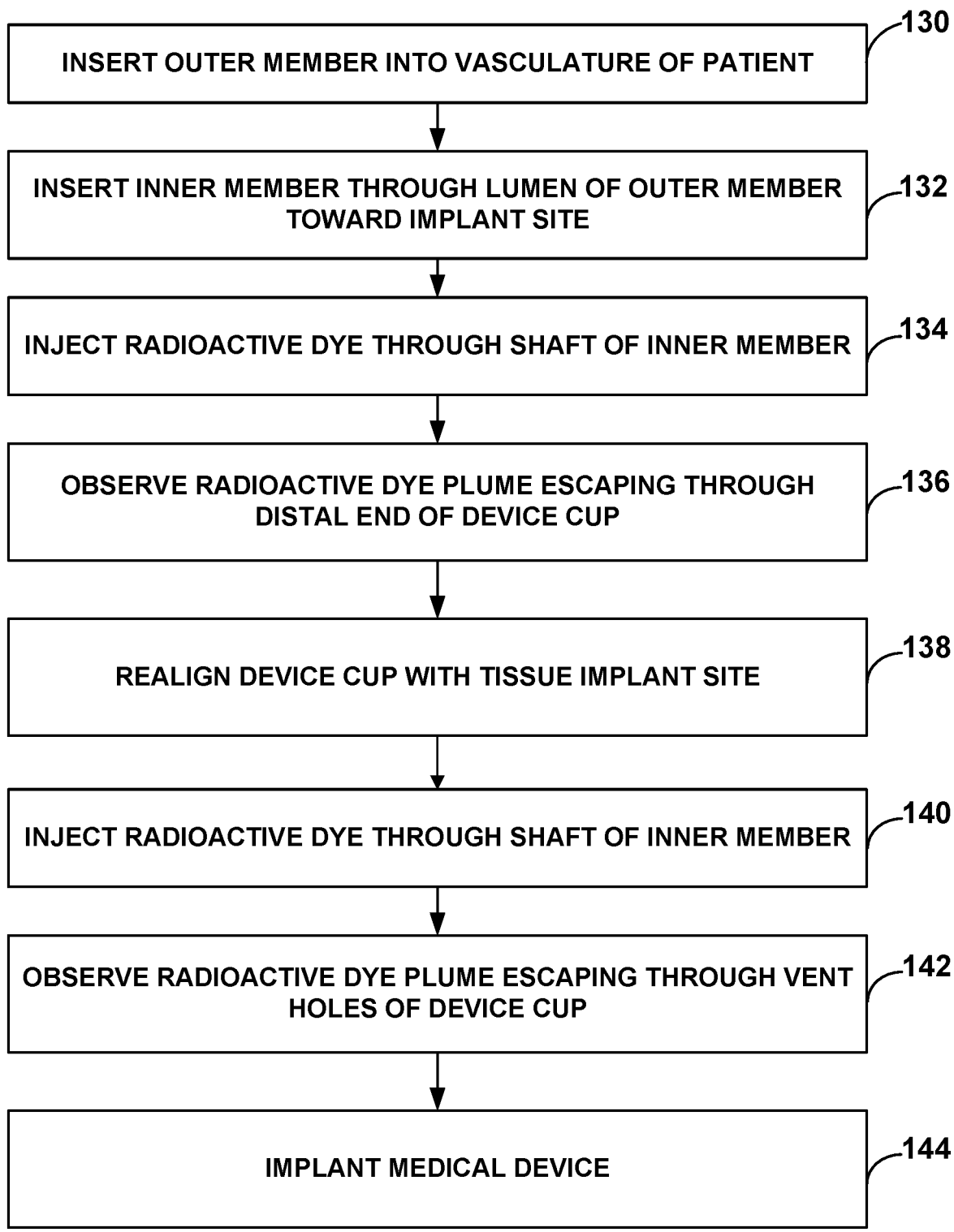
FIG. 13 is a flow chart illustrating an example method of delivering an IMD within a vasculature of a patient, in accordance with some techniques of this disclosure.

FIG. 13 is a flow chart illustrating a method of and implanting an IMD within a vasculature of a patient, in accordance with some techniques of this disclosure. A physician or other qualified operator inserts outer member 16 (such as an introducer) into a vasculature of a patient (130). For example, a physician may insert outer member 16 into a femoral vein of a leg of the patient, and navigate outer member 16 through the patient's vasculature up into the patient's heart. A lumen of outer member 16 then defines a rigid path through the patient's vasculature.

The physician may then insert shaft 12 of inner member 48 (such as a delivery catheter) into the lumen of outer member 16 (132). Through one or more control devices 52 on proximal handle 14, the physician may navigate distal end 44 of inner member 48 through the lumen of outer member 16 toward a tissue implant site 36.

Once the physician has determined that distal end 44 is at or near tissue implant site 36, such as via a screen depicting x-ray imagery of the implant site 36, the physician may inject radioactive dye distally through shaft 12 of inner member 48 toward implant site 36 (134). In some cases, distal end 44 of inner member 48 may not yet be adequately aligned with tissue implant site 36. In these cases, the physician may observe the radioactive dye 38 escaping as a plume through the gap between distal end 44 and tissue 36 (136).

Upon observing misalignment, the physician may again realign distal end 44 with tissue 36, such as via controls 52 on handle 14 (138). Once distal end 44 has been successfully realigned with tissue implant site 36, the physician may again inject radioactive dye 38 through shaft 12 of inner member 48 (140). In this case, because distal end 44 is entirely capped by tissue 36, radioactive dye 38 instead escapes through one or more vent holes 28 defined by device cup 18, which the physician may observe on the screen (142). Upon confirming successful alignment of device cup 18 by observing the plume of radioactive dye 38, the physician my proceed to implant medical device 20 within tissue implant site 36.

The following clauses provide some examples of the disclosure.

Clause 1: In some examples, an implantable medical device delivery system includes: an elongate shaft extending from a proximal end of the elongate shaft to a distal end of the elongate shaft, the elongate shaft configured to extend through a vasculature of a patient; and a device cup attached to the distal end of the elongate shaft, the device cup comprising a cylindrical body configured to receive an implantable medical device, wherein the cylindrical body extends from a proximal end of the cylindrical body to a distal end of the cylindrical body, and wherein the cylindrical body includes: an interior surface; an exterior surface; a distal opening at the distal end of the cylindrical body, the distal opening configured for passage of the implantable medical device; and at least one internal rib extending inwardly from the interior surface of the cylindrical body, the rib configured to contact the implantable medical device to frictionally retain the implantable medical device within the device cup.

Clause 2: In some examples of the system of clause 1, the cylindrical body further includes at least one vent hole extending from the exterior surface of the cylindrical body to the interior surface of the cylindrical body, the at least one vent hole configured to allow fluid to pass through the cylindrical body.

Clause 3: In some examples of the system of clause 2, the at least one vent hole comprises a plurality of vent holes.

Clause 4: In some examples of the system of clause 3, the plurality of vent holes includes at least three vent holes.

Clause 5: In some examples of the system of clause 3 or clause 4, the plurality of vent holes are distributed around a circumference of the cylindrical body.

Clause 6: In some examples of the system of any of clauses 3 to 5, the plurality of vent holes are distributed longitudinally along the cylindrical body.

Clause 7: In some examples of the system of any of clauses 2 to 6, the at least one vent hole is nearer the proximal end of the cylindrical body than the distal end of the cylindrical body.

Clause 8: In some examples of the system of any of clauses 2 to 7, the at least one vent hole is configured to allow increased flow of fluid from inside the cylindrical body in response to the distal opening being covered.

Clause 9: In some examples of the system of any of clauses 2 to 8, the at least one vent hole is configured to channel a radioactive dye when the distal end of cylindrical body is disposed against a tissue of a patient such that the distal opening is covered by the tissue.

Clause 10: In some examples of the system of any of clauses 2 to 9, the at least one vent hole is located over an electrode of the implantable medical device and is configured to allow bodily fluid to contact the electrode when the implantable medical device is retained within the device cup.

Clause 11: In some examples of the system of any of clauses 2 to 10, the cylindrical body further includes at least one external channel.

Clause 12: In some examples of the system of clause 11, the at least one external channel includes a plurality of external channels.

Clause 13: In some examples of the system of clause 11 or clause 12, the plurality of external channels are distributed about a circumference of the cylindrical body.

Clause 14: In some examples of the system of any of clauses 11 to 13, the at least one external channel extends longitudinally from the proximal end of the cylindrical body.

Clause 15: In some examples of the system of any of clauses 11 to 14, the at least one vent hole extends through the at least one external channel.

Clause 16: In some examples of the system of clause 15, the at least one external channel is configured to direct fluid external to the cylindrical body to the at least one vent hole.

Clause 17: In some examples of the system of clause 15 or clause 16, the system further includes an outer member defining a lumen; and an inner member configured to fit inside the lumen, the inner member including the elongate shaft and the device cup, wherein the external channel is configured to direct a bodily fluid through the at least one vent hole and out of the distal end of the cylindrical body when the inner member moves through the lumen of the outer member.

Clause 18: In some examples of the system of any of clauses 1 to 17, the at least one internal rib includes a plurality of internal ribs.

Clause 19: In some examples of the system of clause 18, the plurality of internal ribs are distributed about a circumference of the cylindrical body.

Clause 20: In some examples of the system of clause 18 or clause 19, the plurality of ribs includes at least three ribs.

Clause 21: In some examples of the system of any of clauses 1 to 20, the at least one internal rib extends longitudinally from the proximal end of the cylindrical body.

Clause 22: In some examples of the system of any of clauses 2 to 21, the at least one vent hole extends through the at least one internal rib.

Clause 23: In some examples of the system of any of clauses 1 to 22, the at least one internal rib includes a distal bifurcated structure.

Clause 24: In some examples of the system of clause 23, the distal bifurcated structure includes a distally extending tuning-fork shape.

Clause 25: In some examples of the system of clause 23 or clause 24, the cylindrical body further includes at least one vent hole extending from the exterior surface of the cylindrical body to the interior surface of the cylindrical body, the at least one vent hole configured to allow fluid to pass through the cylindrical body, and wherein the distal bifurcated structure defines an internal channel, the at least one vent hole is located within the internal channel, and the internal channel is configured to direct fluid inside the cylindrical body to the at least one vent hole.

Clause 26: In some examples of the system of any of clauses 1 to 25, the implantable medical device is a pacemaker.

Clause 27: In some examples, a method includes using a medical device delivery system, the system including: an elongate shaft including a proximal end and a distal end; and a device cup attached to the distal end of the elongate shaft, the device cup including a cylindrical body configured to receive an implantable medical device, the cylindrical body including at least one vent hole disposed proximally of a distal end of the device cup; and the method including: introducing the distal end of the elongate shaft into a vasculature of a patient toward a tissue implant site; distally injecting a radioactive dye through the elongate shaft; observing the radioactive dye exiting the at least one vent hole; and implanting the implantable medical device at the tissue implant site based on the observation of the radioactive dye exiting the at least one vent hole.

Clause 28: In some examples of the method of clause 27, distally injecting the radioactive dye includes distally injecting the radioactive dye a second time, the method further including, prior to distally injecting the radioactive dye the second time: distally injecting the radioactive dye through the elongate shaft a first time; observing the radioactive dye exiting the distal end of the device cup; and realigning the distal end of the device cup with the tissue implant site.

Clause 29: In some examples of the method of clause 27 or clause 28, the method further includes proximally withdrawing the elongate shaft from the vasculature of the patient through an outer member, wherein during the proximate withdrawal of the elongate shaft, fluid within the outer member flows through the at least one vent hole and out of a distal opening of the device cup.

Various aspects of the disclosure have been described. These and other aspects are within the scope of the following claims.

What is claimed is:

1. An implantable medical device delivery system comprising:
    an elongate shaft extending from a proximal end of the elongate shaft to a distal end of the elongate shaft, the elongate shaft configured to extend through a vasculature of a patient; and
    a device cup attached to the distal end of the elongate shaft, the device cup comprising a cylindrical body configured to receive an implantable medical device, wherein the cylindrical body extends from a proximal end of the cylindrical body to a distal end of the cylindrical body, and wherein the cylindrical body comprises:

an interior surface;

an exterior surface;

a distal opening at the distal end of the cylindrical body, the distal opening configured for passage of the implantable medical device; and at least one internal rib extending inwardly from the interior surface of the cylindrical body, the at least one internal rib configured to contact the implantable medical device, wherein the cylindrical body further defines at least one vent hole extending from the exterior surface of the cylindrical body to the interior surface of the cylindrical body, wherein the at least one vent hole is configured to allow fluid to pass through the cylindrical body, wherein the at least one internal rib comprises a distal bifurcated structure, wherein a long dimension of the distal bifurcated structure is substantially parallel with a longitudinal axis of the device cup, and wherein the distal bifurcated structure defines an internal channel, the at least one vent hole is located within the internal channel, and the internal channel is configured to direct fluid inside the cylindrical body to the at least one vent hole.

2. The system of claim 1, wherein the at least one vent hole comprises a plurality of vent holes.

3. The system of claim 2, wherein the plurality of vent holes comprises at least three vent holes.

4. The system of claim 2, wherein the plurality of vent holes are distributed around a circumference of the cylindrical body.

5. The system claim 2, wherein the plurality of vent holes are distributed longitudinally along the cylindrical body.

6. The system of claim 1, wherein the at least one vent hole is nearer the proximal end of the cylindrical body than the distal end of the cylindrical body.

7. The system of claim 1, wherein the at least one vent hole is configured to allow increased flow of fluid from inside the cylindrical body in response to the distal opening being covered.

8. The system claim 1, wherein the at least one vent hole is configured to channel a radioactive dye when the distal end of cylindrical body is disposed against a tissue of a patient such that the distal opening is covered by the tissue.

9. The system of claim 1, wherein the at least one vent hole is located over an electrode of the implantable medical device and is configured to allow bodily fluid to contact the electrode when the implantable medical device is retained within the device cup.

10. The system of claim 1, wherein the cylindrical body further comprises at least one external channel.

11. The system of claim 10, wherein the at least one external channel comprises a plurality of external channels.

12. The system of claim 10, wherein the plurality of external channels are distributed about a circumference of the cylindrical body.

13. The system of claim 10, wherein the at least one external channel extends longitudinally from the proximal end of the cylindrical body.

14. The system of claim 10, wherein the at least one vent hole extends through the at least one external channel.

15. The system of claim 14, wherein the at least one external channel is configured to direct fluid external to the cylindrical body to the at least one vent hole.

16. The system of claim 14, further comprising:

an outer member defining a lumen; and an inner member configured to fit inside the lumen, the inner member comprising the elongate shaft and the device cup, wherein the external channel is configured to direct a bodily fluid through the at least one vent hole and out of the distal end of the cylindrical body when the inner member moves through the lumen of the outer member.

17. The system of claim 1, wherein the at least one internal rib comprises a plurality of internal ribs.

18. The system of claim 17, wherein the plurality of internal ribs are distributed about a circumference of the cylindrical body.

19. The system of claim 17, wherein the plurality of ribs comprises at least three ribs.

20. The system of claim 1, wherein the at least one internal rib extends longitudinally from the proximal end of the cylindrical body.

21. The system of claim 1, wherein the distal bifurcated structure comprises a distally-extending tuning-fork shape.

22. The system of claim 1, wherein the implantable medical device comprises a pacemaker.

23. A method for using a medical device delivery system, the system comprising:

an elongate shaft comprising a proximal end and a distal end; and a device cup attached to the distal end of the elongate shaft, the device cup comprising a cylindrical body configured to receive an implantable medical device, the cylindrical body comprising:

an interior surface;

an exterior surface;

a distal opening at a distal end of the cylindrical body, the distal opening configured for passage of the implantable medical device; and at least one internal rib extending inwardly from the interior surface of the cylindrical body, the at least one internal rib configured to contact the implantable medical device, wherein the cylindrical body further defines at least one vent hole disposed proximally of a distal end of the device cup, wherein the at least one internal rib comprises a distal bifurcated structure, wherein a long dimension of the distal bifurcated structure is substantially parallel with a longitudinal axis of the device cup, wherein the at least one vent hole extends from the exterior surface of the cylindrical body to the interior surface of the cylindrical body, the at least one vent hole configured to allow fluid to pass through the cylindrical body, and wherein the distal bifurcated structure defines an internal channel, the at least one vent hole is located within the internal channel, and the internal channel is configured to direct fluid inside the cylindrical body to the at least one vent hole; and the method comprising:

introducing the distal end of the elongate shaft into a vasculature of a patient toward a tissue implant site;

distally injecting a radioactive dye through the elongate shaft;

observing the radioactive dye exiting the at least one vent hole; and implanting the implantable medical device at the tissue implant site based on the observation of the radioactive dye exiting the at least one vent hole.

24. The method of claim 23, wherein distally injecting the radioactive dye comprises distally injecting the radioactive dye a second time.

25. The method of claim 23, further comprising:
- proximally withdrawing the elongate shaft from the vasculature of the patient through an outer member, wherein during the proximate withdrawal of the elongate shaft, fluid within the outer member flows through the at least one vent hole and out of the distal opening of the device cup.

* * * * *